United States Patent
Khoury

(10) Patent No.: US 7,828,837 B2
(45) Date of Patent: Nov. 9, 2010

(54) VASCULAR ENDOGRAFT

(75) Inventor: Michael D. Khoury, Shelby Township, MI (US)

(73) Assignee: Khoury Medical Devices, LLC.

(*) Notice: Subject to any disclaimer, the term of this patent is extended or adjusted under 35 U.S.C. 154(b) by 814 days.

(21) Appl. No.: 11/337,303

(22) Filed: Jan. 23, 2006

(65) Prior Publication Data
US 2006/0184228 A1 Aug. 17, 2006

Related U.S. Application Data

(60) Provisional application No. 60/653,793, filed on Feb. 17, 2005.

(51) Int. Cl.
*A61F 2/06* (2006.01)
(52) U.S. Cl. .................. 623/1.35; 623/1.16
(58) Field of Classification Search ............ 623/1.35, 623/1.11, 1.27, 1.13, 1.15, 1.16, 1.23
See application file for complete search history.

(56) References Cited

U.S. PATENT DOCUMENTS

| | | | |
|---|---|---|---|
| 5,855,598 A | 1/1999 | Pinchuk | |
| 5,984,955 A * | 11/1999 | Wisselink | 623/1.35 |
| 6,017,363 A * | 1/2000 | Hojeibane | 623/23.7 |
| 6,210,429 B1 | 4/2001 | Vardi et al. | |
| 6,325,826 B1 * | 12/2001 | Vardi et al. | 623/1.35 |
| 6,520,987 B1 | 2/2003 | Plante | |
| 6,599,316 B2 | 7/2003 | Vardi et al. | |
| 6,645,242 B1 * | 11/2003 | Quinn | 623/1.16 |
| 6,652,567 B1 | 11/2003 | Deaton | |
| 6,673,107 B1 | 1/2004 | Brandt et al. | |
| 6,695,875 B2 | 2/2004 | Stelter et al. | |
| 6,811,566 B1 | 11/2004 | Penn et al. | |
| 6,814,752 B1 * | 11/2004 | Chuter | 623/1.35 |
| 6,835,203 B1 | 12/2004 | Vardi et al. | |
| 7,144,421 B2 * | 12/2006 | Carpenter et al. | 623/1.31 |

(Continued)

FOREIGN PATENT DOCUMENTS

EP 0684022 A2 10/1995

(Continued)

*Primary Examiner*—Alvin J. Stewart
(74) *Attorney, Agent, or Firm*—Gifford, Krass, Sprinkle, Anderson & Citkowski, P.C.

(57) ABSTRACT

An endograft for a vessel having a vascular branch extending from the vessel is provided. The endograft includes a main body having a wall separating interior and exterior surfaces and adapted to be inserted within the vessel. The main body is characterized by a single proximal opening and a single terminal opening and at least one aperture extending through the wall. At least one stent is secured to the main body that upon expansion pressure fits the main body into the vessel. An open tunnel is secured to the interior surface of the main body around the main body aperture and secured somewhere along the tunnel length to provide fluid communication between the interior and exterior surfaces of the main body through the aperture and with the vascular branch in proximity to the main body aperture. The tunnel is readily formed independent of an expandable stent. Through the addition of further apertures and tunnels, an endograft is well suited for revascularizing the superior mesenteric artery and renal arteries for the treatment of a suprarenal aortic aneurysm. The insertion of a sleeve positioned partly within the tunnel and extending beyond the exterior surface of the main body into the vascular branch assures continued fluid flow to the vascular branch.

17 Claims, 3 Drawing Sheets

U.S. PATENT DOCUMENTS

| | | |
|---|---|---|
| 2003/0199967 A1 | 10/2003 | Hartley et al. |
| 2004/0133266 A1 | 7/2004 | Clere et al. |
| 2004/0210236 A1 | 10/2004 | Allers et al. |
| 2004/0225345 A1 | 11/2004 | Fischell et al. |
| 2004/0230287 A1 | 11/2004 | Hartley et al. |
| 2004/0260383 A1 | 12/2004 | Stelter et al. |

FOREIGN PATENT DOCUMENTS

| | | |
|---|---|---|
| EP | 0880948 A1 | 1/1998 |
| EP | 0971646 B1 | 9/1998 |
| WO | WO 01/67993 A2 | 9/2001 |
| WO | WO 03/082153 A2 | 10/2003 |

* cited by examiner

VASCULAR ENDOGRAFT

RELATED APPLICATION

This application claims priority of U.S. Provisional Patent Application Ser. No. 60/653,793 filed Feb. 17, 2005, which is incorporated herein by reference.

FIELD OF THE INVENTION

The present invention in general relates to a vascular endograft and method for surgical deployment thereof, and in particular to a vascular endograft facilitating revascularizing branching vessels.

BACKGROUND OF THE INVENTION

Stent grafts have become a popular treatment option for aneurysms. Typically, a stent graft is delivered to a treatment site through endovascular insertion via an introducer or catheter. Subsequent radial expansion retains the graft in position relative to the vessel wall. In instances where an aneurysm is located along a length of vessel on which branch vessels are not present, a simple tubular cylindrical stent graft is suitable. Additionally, stent grafts are known to the art for treatment of aneurysms in aortic regions where the distal end of the graft bifurcates to define two lumens so as to extend into arterial branches. Such bifurcated stent grafts are well known for the treatment of ascending thoracic and abdominal aortic aneurysms. Exemplary stents of this kind are embodied in U.S. Pat. Nos. 6,695,875 B2 and 6,814,752 B1 and U.S. Patent Application Publication 2004/0230287 A1.

Currently, aneurysms in certain anatomic regions of the aorta have proved difficult to properly repair with a stent graft. In particular, treatment of suprarenal aortic aneurysms has proved problematic. In such locales, the lack of a neck above the aneurysm precludes attachment of a conventional endovascular graft. Additionally, in the treatment of an aneurysm in such a locale, the preoperative measurement of arterial and aortic dimensional variables necessary to form a suitable endograft has proven to be complex. Any misfit in preparing a conventional stent graft to treat an aneurysm in this region results in lumenal obstruction or collapse, or material fatigue, resulting in continued blood flow into the aneurysm.

WO 03/082153, FIGS. 7-11, is representative of the stent grafts for the treatment of suprarenal aortic aneurysms. This graft includes a single lumen containing a Gianturco type zigzag Z stent tube in communication at a distal end with an aperture in the lumen and free floating at the proximal end within the lumen. Unfortunately, the free-floating tube proximal end is prone to damage during insertion of a sleeve therefrom into an artery in registry with the aperture, as well as under hemodynamic operating conditions.

Thus, there exists a need for a vascular endograft capable of treating an aneurysm in a vessel having adjacent vessel branches.

SUMMARY OF THE INVENTION

An endograft for a vessel having a vascular branch extending from the vessel is provided. The endograft includes a main body having a wall separating interior and exterior surfaces and adapted to be inserted within the vessel. The main body is characterized by a single proximal opening and a single terminal opening and at least one aperture extending through the wall. At least one stent is secured to the main body that upon expansion pressure fits the main body into the vessel. An open tunnel is secured to the interior surface of the main body around the main body aperture and secured somewhere along the tunnel length to provide fluid communication between the interior and exterior surfaces of the main body through the aperture and with the vascular branch in proximity to the main body aperture. The tunnel is readily formed independent of an expandable stent. Through the addition of further apertures and tunnels, an endograft is well suited for revascularizing the celiac, superior mesenteric artery and renal arteries for the treatment of a suprarenal aortic aneurysm. The insertion of a sleeve positioned partly within the tunnel and extending beyond the exterior surface of the main body into the vascular branch assures continued fluid flow to the vascular branch.

DETAILED DESCRIPTION OF THE PREFERRED EMBODIMENTS

The present invention has utility as a vascular endograft well suited for the treatment of aneurysms. While the present invention is detailed herein with respect to an endograft having revascularization tunnels positioned for use in the aortic region encompassing the superior mesenteric artery (SMA) and renal arteries, it is appreciated that an inventive endograft has application in a variety of vascular settings where vessels branch from a main lumen. In addition, the inventive endograft is appreciated to be suitable for the treatment of an aneurysm alone, or in combination with a conventional stent graft depending upon the relative position and size of a vascular aneurysm.

An inventive endograft has a main body including at least one deployable, expanding stent and an open tunnel secured within the main body to a main body sidewall aperture to ensure reliable fluid communication between fluid passing through the main body and a vascular branch overlying an open tunnel terminus. The tunnel is secured somewhere along the tunnel length to the interior of the main body and lacks a stent expander along the length thereof. Preferably, the tunnel is secured to the main body along the majority of the tunnel length. Through the use of a sleeve that extends from the tunnel into the overlying vascular branch, a predefined percentage of the fluid flow through the main body of an inventive endograft is shunted into the vascular branch. While an open tunnel used in an inventive endograft is cylindrical in general shape in a first embodiment, it is appreciated that a bifurcated tunnel having an inverted "Y" shape is operative in situations where vascular branch bifurcates proximal to the central vessel are desired to have assured fluid flow.

Figure 1:
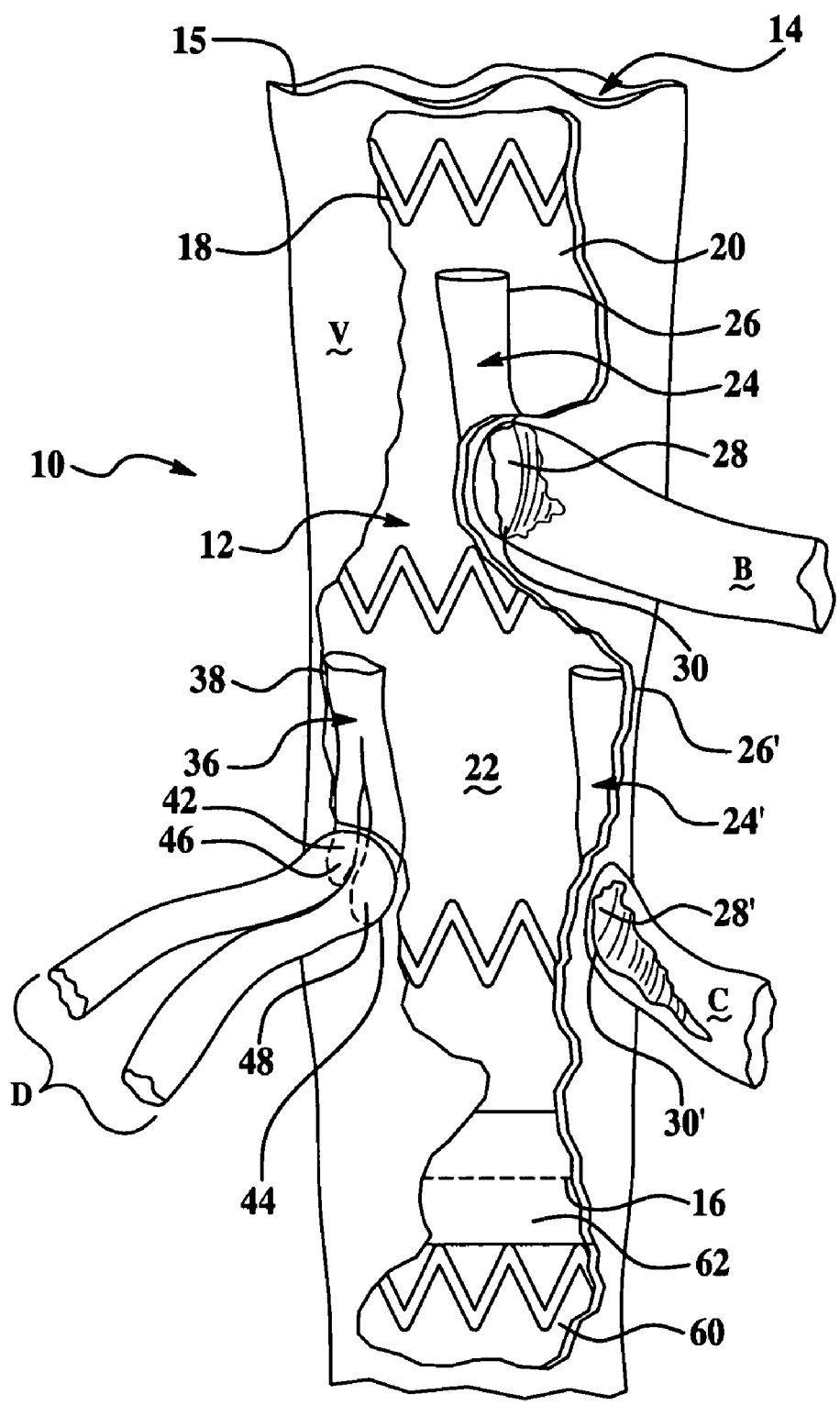
FIG. 1 is a plan view of an inventive endograft depicted within a partial cutaway of the superior mesenteric and renal artery region of the descending aorta.
Figure 2:
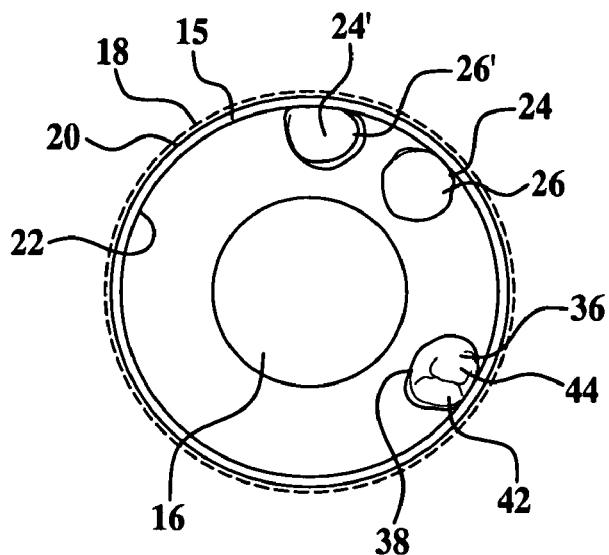
FIG. 2 is a top view of the inventive stent graft depicted in FIG. 1 absent the expandable stents for visual clarity.
Figure 3:
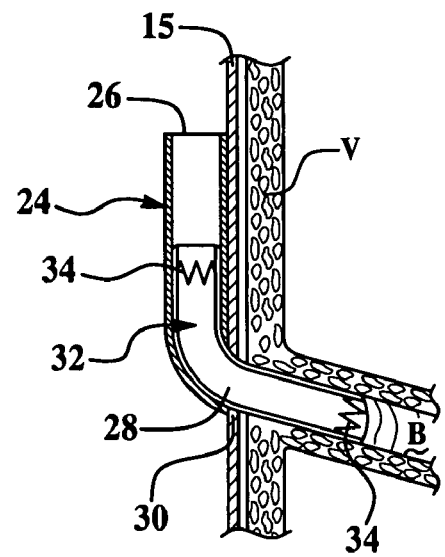
FIG. 3 is a magnified cross-sectional view through a tunnel connecting the endograft depicted in FIG. 1 to the superior mesenteric artery and containing a sleeve therein.
Figure 4:
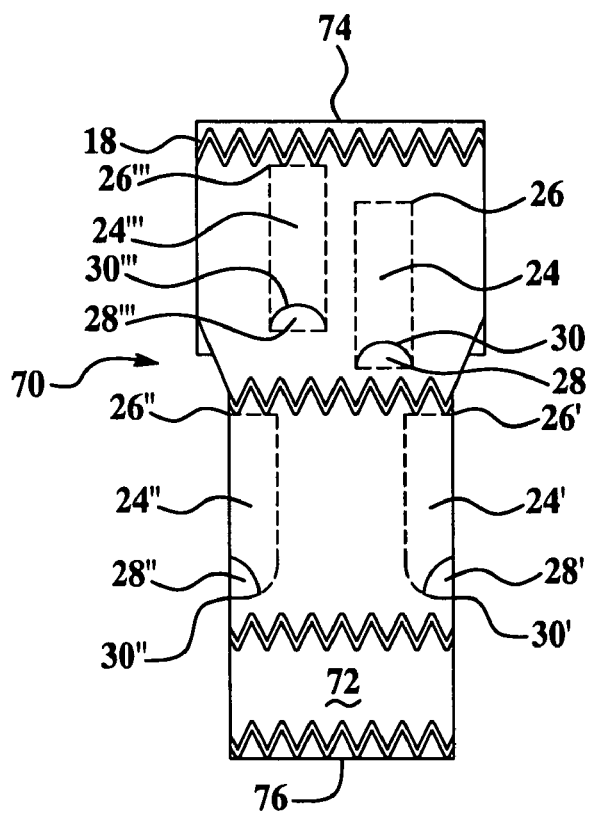
FIG. 4 is a plan view of an inventive endograft proportioned and apertured for revascularization of the celiac, superior mesenteric, and two renal arteries, the tunnels are depicted interior to the endograft as dashed lines; the expandable Z stents are not shown for visual clarity.

The present invention is further illustrated with respect to the following non-limiting embodiments depicted in the figures. Referring now to FIGS. 1-3, an inventive endograft is shown generally at 10. The endograft 10 has a main body 12 having at least one proximal opening 14 and at least one distal opening 16. As used herein, it is appreciated that proximal and distal are defined relative to the direction of fluid flow through the vessel lumen in which an inventive endograft is secured. At least one stent 18 is secured about the circumference of the main body 12 on the external surface 20 of the main body wall 15. A Gianturco zigzag stent is representative of stent types operative herein. The main body 12 has an interior surface 22 through which fluid communication within the vessel is maintained. An open tunnel 24 has a mouth 26 and a terminus 28. The tunnel 24 is formed of a material that will not become obstructed or collapse under prolonged exposure to physiologic fluid transport. Materials suitable for the construction of a main body 12 and a tunnel 24 independently in each case include polymeric materials such as those sold under the trade names Dacron®, Gortex®, Teflon® and implant grade silicones. In order to preclude obstruction and/or collapse of a tunnel 24 subsequent to placement, the tunnel 24 is formed independent of an extendable stent associated with the tunnel circumference. The terminus 28 of the tunnel 24 is sealed around an aperture 30 within the main body 12 and is flush with the exterior surface 20. As a result, the tunnel 24 does not extend beyond the dimensions of the main body 12; this attribute facilitates placement of an inventive endograft 10 within the central vessel denoted at V. The tunnel 24 preferably has a uniform cross-sectional area between the mouth and along the tunnel length. The aperture 30 and terminus 28 of the tunnel 24 are positioned within the main body 12 so as to overlie a vascular branch B extending from the vessel V in which the main body 12 is placed. The tunnel 24 is secured to the interior surface 22 at at least one point along the tunnel length. A single point securement is ideally proximal to the mouth 28. Preferably, the tunnel is secured along the majority of the tunnel length. More preferably, the entire tunnel length is secured to the interior surface 22. Securement of the tunnel 24 to the interior surface 22 is accomplished with conventional fastening techniques illustratively including sutures, contact adhesives, sonic welding, thermal welding, and combinations thereof. A securement anchoring the tunnel 24 to the interior surface 22 is critical to the longevity of an inventive endograft in assuring that the tunnel 24 does not kink during placement or under the strong pulsatile flow dynamics experienced within the aorta. It is appreciated that each vascular branch requiring perfusion that overlies an inventive endograft is provided with an open tunnel as described herein to assure fluid communication therewith.

With an inventive endograft 10 placed within a vessel V, fluid communication with a vascular branch B is provided through the placement of a separate sleeve 32 in part within the tunnel 24 and extending beyond the terminus 28 into the vascular branch B as shown in FIG. 3. A sleeve 32 is conventional to the art and typically is formed of materials such as those used for the formation of the main body 12 or the tunnel 24. A sleeve 32 typically includes multiple circumferential stents 34 in order to retain the sleeve 32 in a preselected position relative to the tunnel 24 and the vascular branch B.

The inventive embodiment depicted in FIGS. 1-3 corresponds to an endograft spanning the suprarenal portion of the aorta and as such the vessel V is the aorta and the vascular branch B is the superior mesenteric artery. The additional vascular branches depicted at C and D correspond to the right and left renal arteries, respectively. As blood flow to the renal arteries C and D must necessarily be maintained in a successful aneurysm treatment, tunnel 24' is placed within the main body 12 in order to assure fluid communication between the aorta and the right renal artery C, where like primed numerals correspond to those detailed above with respect to tunnel 24. Tunnel 24 is secured to the interior surface 22 as detailed above with respect to tunnel 24. The left renal artery D is depicted with the uncommon phenotype of an immediate bifurcation in order to illustrate that a bifurcated tunnel 36 optionally replaces a cylindrical tunnel as depicted with reference to numeral 24 in instances where patient anatomy so dictates. Bifurcated tunnel 36 has a mouth 38 of a preselected diameter and a bifurcation 40 so as to define a first terminus 42 and a second terminus 44. The termini 42 and 44 are sealed to apertures 46 and 48 formed through the wall 15 of the main body 12. Tunnel 36 is secured to the interior surface 22 as detailed above with respect to tunnel 24. Sleeves 50 and 52 are similar to sleeve 32 as described with respect to tunnel 24 and serve to assure a preselected percentage of blood flow to each of the left renal arterial branches.

It is appreciated that the relative percentage of fluid exiting through an inventive tunnel relative to the percentage of fluid exiting the distal opening of an inventive endograft is controlled by the effective diameter of the tunnel as compared to the endograft diameter at the position of the tunnel mouth. The effective diameter of an inventive tunnel is appreciated to be equivalent to the internal diameter of the tunnel mouth in the theoretical instance where the tunnel wall and sleeve are of infinitesimal thickness. Actual flow to a vascular branch is readily modeled with standard fluid dynamic equations. In the embodiment depicted in FIGS. 1-3, tunnels 24, 24' and 36 have lengths ranging from 10 to 25 millimeters with each tunnel having a diameter of from between 6 and 12 millimeters. The internal surface diameter at the proximal opening 14 is typically between 35 and 45 millimeters while the internal diameter about the distal opening 16 ranges from 20 to 30 millimeters. The overall length of the endograft 10 for an adult human ranges from 60 to 120 millimeters. While the above dimensional ranges associated with an inventive endograft 10 are those associated with a suprarenal endograft for an adult human subject, it is appreciated that human child, veterinary endografts, as well as those used to treat differently positioned aneurysms within an adult human, or to accommodate peculiar subject anatomy will vary in any, or all of these dimensions.

An inventive endograft in addition to itself precluding fluid flow to an aneurysm is appreciated to be suitable for the joinder of a secondary stent 60 to the distal opening 16 thereof in order to function as an anchoring neck for a conventional stent graft. Joinder of a secondary stent 60 to an inventive endograft is accomplished through a variety of techniques including the use of a vascular cuff 62.

In selecting an endograft for a particular individual, the principal variables include measurement of the internal diameter of the vessel that provides the outer diameter of an inventive endograft, as well as the tunnel terminus internal diameter derived from a measurement of vascular branch internal diameter. Compared to existing stent grafts, the present invention represents a simplification of the design modifications and overall preoperative measurements associated with stent graft design.

The placement of an inventive endograft optionally results in the sacrifice of the celiac artery in the instance where the inventive endograft is in a suprarenal position. While an inventive endograft is extended to provide a tunnel for the celiac artery, the celiac artery sacrifice is compensated for by continued flow through the superior mesenteric artery to prevent adverse events. Sacrifice of the celiac artery provides a considerably longer sealing zone proximal to mouth 26 of the tunnel 24. The suprarenal endograft 10 depicted in FIGS. 1-3 is an indicated treatment for individuals with pararenal or suprarenal abdominal aortic aneurysms, as well as those individuals suffering failure of a conventional endograft repair secondary to aortic neck deterioration.

An endograft maintaining flow to an overlying celiac artery is depicted in plan view generally at 70, where like numerals correspond to those detailed with respect to FIG. 1. The endograft 70 has tunnels 24 and 24' having termini 28 and 28' that are spaced to overlie the aortic junctions with the superior mesenteric and right renal arteries, respectively, upon implantation. Additional tubular tunnels 24" and 24'" are provided with termini 28" and 28'" that are spaced to overlie the left renal and celiac arteries, respectively, upon implantation. Each of the tunnels 24, 24', 24", and 24'" has a mouth 26, 26', 26", and 26'", and are secured to the interior surface of the main body wall 72, as described with respect to FIGS. 1-3. A portion of the fluid entering the proximal opening 74 relative the direction of fluid flow through the vessel lumen in which an inventive endograft is secured is communicated through the main body 12, past at least one stent 18 and into one of the tunnels 24, 24', 24", or 24'" and expelled via one of the apertures 30, 30', 30", or 30'" extending through the main body wall 72. The fluid not transiting the wall 72 is expelled via distal opening 76.

A procedure for repair of a renal aneurysm is preferably performed in a staged fashion to decrease the overall time of the procedure, fluoroscopy contrast agent exposure, and radiation dosage. An exemplary procedure for placement of an inventive endograft as a repair includes the following steps.

1. CT Assessment: Identify patient candidates and obtain diameter and length measurements. Initial assessment with high resolution helical CT scans will identify patients that are candidates for this procedure. The CT protocol will be similar to infrarenal stent graft assessments, but extend from the distal descending thoracic aorta to the common femoral arteries. In patient candidates aortic diameters and lengths will be determined.

2. Angiography and visceral artery covered stent placement. Diagnostic angiography will provide further anatomic definition, also covered stents will be deployed in the SMA and the right and left renal arteries. Patient candidates identified with CT will proceed to angiography to assess the status of the SMA and renal arteries. In addition, any stenotic lesions of the visceral arteries will be treated at this time.

3. Endograft deployment, mesenteric revascularization, conventional endograft aneurysm repair. The delivery and deployment of the aortic endograft will utilize the current methods used with infrarenal aneurysm endograft repair. Bilateral femoral artery exposure and left brachial artery access will be used. The patient will be anticoagulated once artery exposure is obtained.

Endograft deployment: A stiff guide wire is advanced under fluoroscopy into the proximal descending thoracic aorta from the femoral artery being used for delivery of the main aortic component. The main component is then delivered into the distal descending thoracic aorta for deployment above the SMA, using the previously placed SMA covered stent as a landmark. The endograft will be oriented by unique radio-opaque markers for the renal and SMA branches. Once in position the supra mesenteric component will be partially deployed for a length of about 2.5 centimeters or otherwise to expose the celiac and SMA upstream apertures 30'" and 30, respectively, as shown in lateral view in FIG. 5A. The infrarenal portion of the endograft will not be deployed until mesenteric revascularization is complete to avoid compromising guide wire access to the native mesenteric arteries.

Figure 5C:
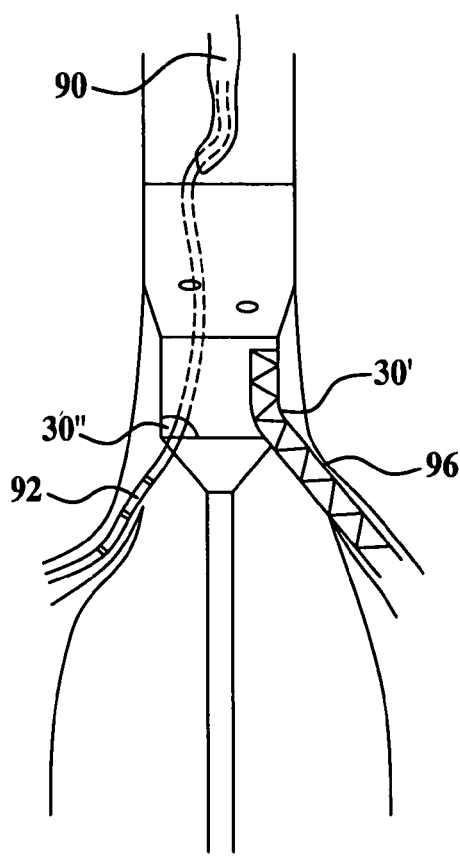
FIGS. 5A-5D are a schematic depiction of a possible surgical process for revascularizing celiac, superior mesenteric, and renal arteries, as part of the deployment of an inventive endograft to treat a suprarenal aortic aneurysm.
Figure 5D:
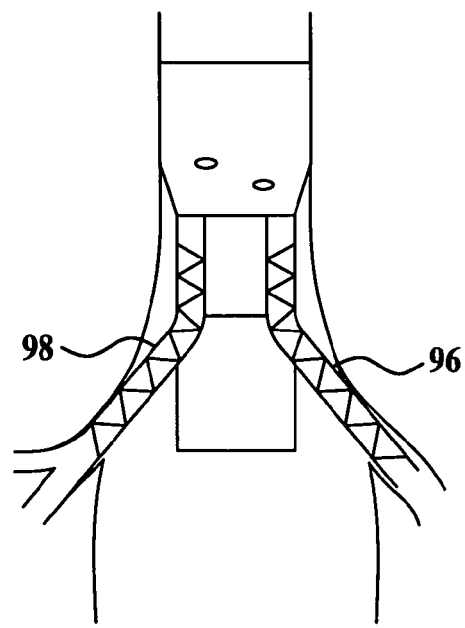
Figure 5A:
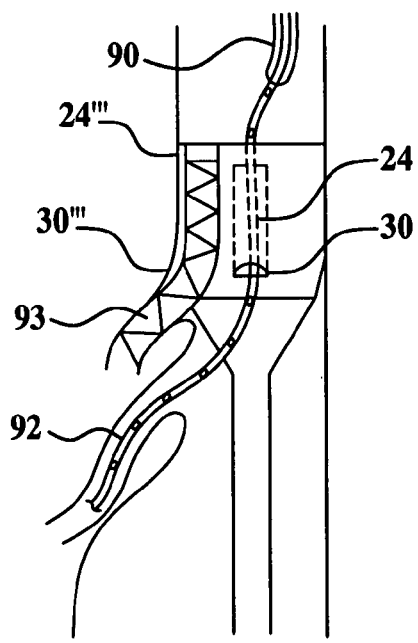
Figure 5B:
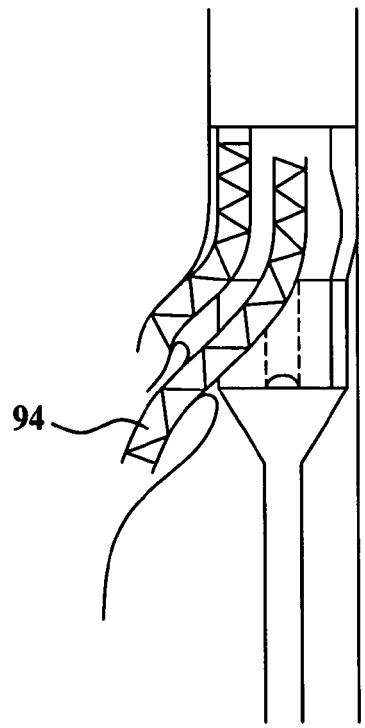

4. Visceral revascularization. Placing the mesenteric endografts will optimally be performed from the left brachial approach. This will take advantage of the visceral artery anatomy relative to the aorta. Using standard guide wire techniques a 90 centimeter brachial catheter 90 sheath is advanced to the aorta proximal to the endograft. The SMA tunnel will be accessed within the endograft by a marking catheter 92 having gradations to assess the required sleeve length needed to extend within the endograft and into the branching vessel to which fluid communication is to be maintained. The marking catheter 92 will be advanced through the tunnel into the native aortic lumen and into the native SMA. A stent is then fed into position spanning a portion of the tunnel 24 through aperture 30 and into the native SMA before sleeve stent expansion 94 in FIG. 5B. In FIG. 5A the celiac artery is shown having already been spanned by a sleeve stent 93 expanded in tunnel 24'" and extending through aperture 30'" into the native celiac artery by a process as detailed above for the SMA. The order of SMA and celiac artery revascularization is appreciated to be immaterial. Typically, a stent has at least 1.5 centimeter coverage into the native artery. Alternatively, the celiac and/or SMA spanning stents are transported up the given artery into the appropriate sleeve. Proximity to an aneurysm or an involved arterial juncture are instances that are indications that may justify the added complexity of arterial stent delivery. The positioning of the endograft or the sleeve stent is guided with contrast injections from the brachial catheter 90.

Subsequent to SMA and optional celiac artery revascularization, as the visceral first stage of endograft deployment, longitudinal expansion of the endograft main body occurs distal from aperture 30. It is noted that revascularizing the SMA and optional celiac artery affords a measure of fixation to the endograft against torsion associated with succeeding renal artery revascularization.

This procedure will be repeated for the right and left renal arteries. Once SMA and renal endovascular revascularization is completed the infrarenal component of the SRE will be deployed. This completes SRE deployment and visceral revascularization.

5. Renal revascularization. FIGS. 5C and 5D are rotated views relative to the lateral views of FIGS. 5A and 5B to schematically illustrate renal artery revascularization. The brachial catheter 90 and the marking catheter 92 are employed as detailed above for visceral SMA revascularization to successively revascularize the right and left renal arteries with sleeves 96 and 98, respectively. Preferably, the distal 2.5 centimeter section of the endograft main body is retained in a collapsed state during positioning and expansion of sleeves 96 and 98. Thereafter, as shown in FIG. 5D, the distal docking end of the endograft is expanded.

6. Distal joinder. Additional joinder of a secondary conventional stent to the distal end of the endograft then occurs in instances where additional length is required to span an aneurysm. A secondary stent is deployed directly to the distal end or with resort to a vascular cuff.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. An endograft for a vessel having a vascular branch extending from the vessel, said endograft comprising:
a main body having a wall defining an internal surface and an exterior surface and adapted to be placed within the vessel, the wall defining a single lumen at a proximal end and a single lumen at a terminal end of said main body, and a main body aperture extending from the interior surface to the exterior surface at least one expandable stent secured to said main body; and an open tunnel independent of an expandable stent associated with a circumference of said runnel and having a length extending between a mouth and a terminus, said tunnel having a uniform cross-sectional area between the mouth and along the length to the terminus, the terminus of said runnel sealed to the interior surface of said main body about the main body aperture, said tunnel secured along a majority of the tunnel length to the internal surface to provide fluid communication between the interior surface and the exterior surface through the main body aperture and with the vascular branch in proximity to the main body aperture, wherein the terminus of said tunnel is flush with the external surface of said main body.

2. The endograft of claim 1 wherein the vessel is the descending aorta and the vascular branch is the superior mesenteric artery.

3. The endograft of claim 1 wherein said tunnel bifurcates to create a second terminus defining a second main body aperture.

4. The endograft of claim 1 further comprising a sleeve positioned partly within said tunnel and extending beyond the exterior surface of said main body into the vascular branch, said sleeve concentric with the main body aperture.

5. The endograft of claim 1 further comprising at least one additional open tunnel within said main body.

6. The endograft of claim 5 wherein in said at least one additional open tunnel are two additional open tunnels.

7. The endograft of claim 6 wherein the terminus of said open tunnel is positioned on said main body such that upon insertion into a subject, the terminus overlies the superior mesenteric artery and said two additional open tunnels overlie the renal arteries.

8. The endograft of claim 7 wherein said at least one stent comprises a first stent proximal to the proximal end of said main body and proximal to the mouth of said tunnel, a second stent distal from the main body aperture and proximal to said two additional open tunnels, and a third stent disposed distal to said two additional open tunnels.

9. The endograft of claim 1 wherein said tunnel has an internal diameter of between 6 and 12 millimeters.

10. The endograft of claim 1 wherein said tunnel has a length of from 10 to 25 millimeters.

11. The endograft of claim 1 further comprising a secondary stent coupled to said main body.

12. The endograft of claim 11 further comprising a vascular cuff in simultaneous contact with said main body and said secondary stent.

13. An endograft for a vessel having a vascular branch extending from the vessel, said endograft comprising:
a main body having a wall defining an internal surface and an exterior surface and adapted to be placed within the vessel, the wall defining a single lumen at a proximal end and a terminal end of said main body, mad a main body aperture extending from the interior surface to the exterior surface;
at least one expandable stent secured to said main body; and an open tunnel independent of a stent associated with a circumference of said tunnel and having a runnel length extended between a mouth and a terminus, said tunnel sealed along all of the tunnel length to the interior surface of said main body the terminus of said tunnel sealed about the body aperture to provide fluid communication between the interior surface and the exterior surface through the main body aperture and with the vascular branch in proximity to the main body aperture, wherein the terminus of said tunnel is flush with the external surface of said main body.

14. The endograft of claim 13 wherein the vessel is the descending aorta and the vascular branch is the superior mesenteric artery.

15. The endograft of claim 13 wherein the terminus of said tunnel is positioned on said main body such that upon insertion into a subject, the terminus overlies the superior mesenteric artery and further comprising two additional open tunnels that overlie the renal arteries.

16. The endograft of claim 15 wherein said at least one stent comprises a first stent proximal to the proximal end of said main body and proximal to the mouth of said tunnel, a second stent distal from the main body aperture and proximal to said two additional open tunnels, and a third stent disposed distal to said two additional open tunnels.

17. The endograft of claim 13 further comprising a sleeve positioned partly within said tunnel and extending beyond the exterior surface of said main body into the vascular branch, said sleeve concentric with the main body aperture.

* * * * *